US010390830B2

(12) United States Patent
Schulz

(10) Patent No.: US 10,390,830 B2
(45) Date of Patent: Aug. 27, 2019

(54) SURGICAL CLIP APPLICATOR

(71) Applicant: Aesculap AG, Tuttlingen (DE)

(72) Inventor: Peter Schulz, Löffingen (DE)

(73) Assignee: Aesculap AG (DE)

( * ) Notice: Subject to any disclaimer, the term of this patent is extended or adjusted under 35 U.S.C. 154(b) by 126 days.

(21) Appl. No.: 14/897,976

(22) PCT Filed: Jun. 12, 2014

(86) PCT No.: PCT/EP2014/062193
§ 371 (c)(1),
(2) Date: Dec. 11, 2015

(87) PCT Pub. No.: WO2014/202449
PCT Pub. Date: Dec. 24, 2014

(65) Prior Publication Data
US 2016/0113652 A1 Apr. 28, 2016

(30) Foreign Application Priority Data
Jun. 17, 2013 (DE) .................. 10 2013 106 277

(51) Int. Cl.
*A61B 17/10* (2006.01)
*A61B 17/128* (2006.01)
(Continued)

(52) U.S. Cl.
CPC .......... *A61B 17/105* (2013.01); *A61B 17/128* (2013.01); *A61B 2017/0023* (2013.01);
(Continued)

(58) Field of Classification Search
CPC ............... A61B 17/105; A61B 17/128; A61B 2017/0046; A61B 2017/292;
(Continued)

(56) References Cited

U.S. PATENT DOCUMENTS 4,509,518 A * 4/1985 McGarry ............ A61B 17/128
606/143
4,611,595 A  9/1986 Klieman
(Continued)

FOREIGN PATENT DOCUMENTS

CN 102090911 A 6/2011
CN 102327136 A 1/2012
(Continued)

OTHER PUBLICATIONS

English Translation of PCT Written Opinion of the International Searching Authority for PCT/EP2014/062193 dated Apr. 2, 2015.
(Continued)

*Primary Examiner* — Tuan V Nguyen
(74) *Attorney, Agent, or Firm* — RatnerPrestia

(57) ABSTRACT

A surgical clip applicator includes a universal handgrip and an individual clip magazine having an integrated crimping head, which individual clip magazine can be detachably fastened to the universal handgrip. The universal handgrip and the individual clip magazine fastened thereto interact to form a feed path for the clip transport of individual clips from a clip receiving portion of the clip magazine toward the crimping head, which feed path is defined or individually available for actuation. The individual clip magazine can be selected from a plurality of clip magazines for different clip types as needed. The clip magazine can include an integrated coding mechanism designed depending on the clip type to be applied, which coding mechanism defines in interaction with the universal handgrip at least the feed path adapted to the respective clip type.

11 Claims, 5 Drawing Sheets

Figure 1:
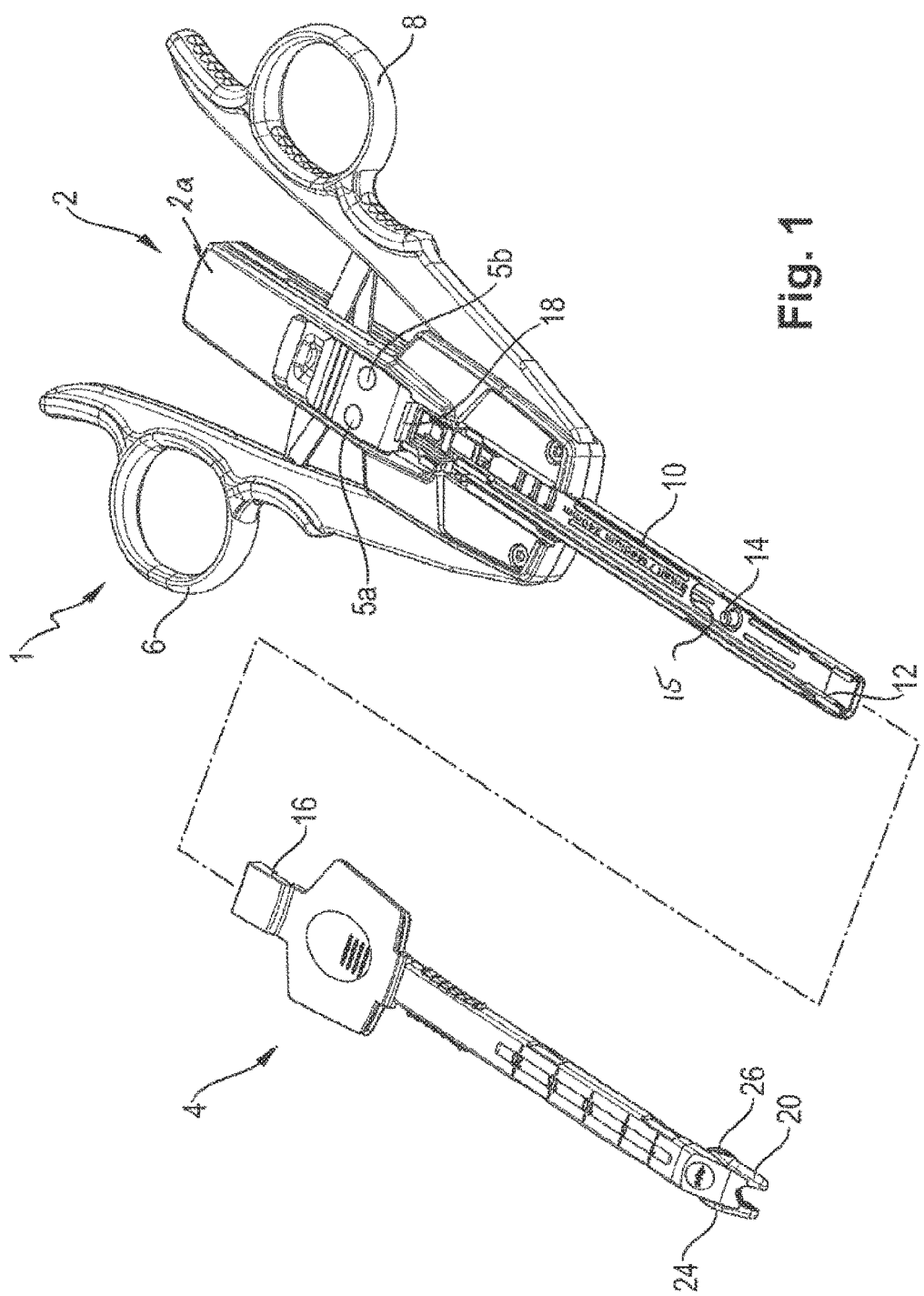

(51) Int. Cl.
    *A61B 17/00* (2006.01)
    *A61B 17/29* (2006.01)
    *A61B 90/00* (2016.01)

(52) U.S. Cl.
    CPC .......... *A61B 2017/0046* (2013.01); *A61B 2017/00424* (2013.01); *A61B 2017/00482* (2013.01); *A61B 2017/292* (2013.01); *A61B 2090/032* (2016.02); *A61B 2560/0443* (2013.01)

(58) Field of Classification Search
    CPC .... A61B 2017/00482; A61B 2090/032; A61B 2560/0443
    See application file for complete search history.

(56) References Cited

U.S. PATENT DOCUMENTS

| | | | |
|---|---|---|---|
| 6,599,298 | B1 | 7/2003 | Forster |
| 6,699,255 | B1 | 3/2004 | Cushchieri |
| 9,636,128 | B2 | 5/2017 | Zemlolk et al. |
| 2004/0153100 | A1 | 8/2004 | Ahlberg et al. |
| 2008/0083813 | A1 | 4/2008 | Zemlok |
| 2010/0137886 | A1 | 6/2010 | Zergiebel |
| 2011/0024145 | A1 | 2/2011 | Click |
| 2011/0137323 | A1* | 6/2011 | Malkowski .......... A61B 17/068 606/143 |
| 2013/0240599 | A1* | 9/2013 | Scirica ............ A61B 17/07207 227/176.1 |
| 2014/0005696 | A1 | 1/2014 | Schulz et al. |
| 2016/0030045 | A1 | 2/2016 | Malkowski et al. |
| 2017/0027581 | A1 | 2/2017 | Zergiebel et al. |

FOREIGN PATENT DOCUMENTS

| | | |
|---|---|---|
| DE | 4429084 | 6/1995 |
| DE | 69807725 | 6/2003 |
| DE | 202011000755 | 6/2011 |
| JP | 2007530222 A | 11/2007 |
| JP | 2013027722 A | 2/2013 |
| RU | 2362498 | 7/2009 |
| WO | 9922650 A2 | 5/1999 |
| WO | 0042922 | 7/2000 |
| WO | 2005099592 A1 | 10/2005 |
| WO | 2012130589 A1 | 10/2012 |

OTHER PUBLICATIONS

German Search Report for German Application No. 10 2013 106 277.6 dated Feb. 26, 2014, with partial translation.
International Search Report of International Application No. PCT/EP2014/062193 dated Apr. 2, 2015.
Partial Search Report for International Application No. PCT/EP2014/062193 dated Nov. 27, 2014, with partial translation attached.
Chinese Office Action for Chinese Application No. 201480032499.2, dated Jul. 31, 2017, including English translation, 20 pages.
Chinese Office Action for Chinese Application No. 201480032499.2, dated Jun. 5, 2018, with English translation, 24 pages.
Notifiction of Reasons for Rejection for Japanese Application No. 2016-518484, dated Feb. 20, 2018 with translation, 12 pages.

* cited by examiner

SURGICAL CLIP APPLICATOR

RELATED APPLICATIONS

This application is the U.S. National Phase of International Application No. PCT/EP2014/062193, filed Jun. 12, 2014, which claims the benefit of priority of German Application No. 10 2013 106 277.6, filed Jun. 17, 2013. The contents of International Application No. PCT/EP2014/062193 and German Application No. 10 2013 106 277.6 are incorporated by reference in their entireties and for all purposes.

FIELD

The invention relates to a surgical clip applicator, a clip magazine for said clip applicator as well as a handgrip for detachably receiving the clip magazine.

BACKGROUND

Clip applicators are surgical instruments setting (applying) tissue clips on the tissue of a patient, for instance for closing a seam or a vessel. This avoids an expensive suturing process, which is advantageous in particular in case of operation sites which are difficult to access from outside.

A generic clip applicator is known, for instance, from DE 20 2011 000 755 U1. This kind of clip applicator can be used in open and endoscopic surgery for quickly and reliably connecting tissue structures of a patient, who has to be operated, by applying and subsequently closing preferably U-shaped or V-shaped clips. Such a clip applicator may be especially used to pinch off blood vessels of a patient in short time and in a reliable manner. Different clip types can be used here, which may differ from one another in terms of their shape, but also in size and thickness.

The clip applicator described in document DE 20 2011 000 755 U1, whose disclosure content is incorporated hereby in the subject-matter of the present application, comprises a handgrip part to which a clip magazine having an integrated clip storage means can be fastened in detachable fashion. In this arrangement, the handgrip part is provided and correspondingly arranged to be used several times as a reusable part. In contrary, the clip magazine is provided and correspondingly arranged to be used as a disposable part only until the clips stored in the clip storage means of the clip magazine are used up.

Although this clip applicator can be made available at comparably low costs and also allows a comparatively safe way of applying and closing the clips, it would be desirable to improve the handling of the clip applicator. This desire results from the fact that the handgrip part of this clip applicator is merely provided to be combined with clip magazines of the same design, the same clip type and the same clip size. In other words, only one clip type can be applied with one and the same handgrip part, despite the replacement of individual clip magazines. This means that a plurality of various handgrip parts as well as a plurality of different clip magazines perhaps have to be kept available in the surgery room, and any combination of handgrip part and clip magazine can be used only for a single clip type. This, however, is disadvantageous in terms of the spatial conditions and the clarity in the surgery room.

Another prior art is described in DE 44 29 084 C1. The clip applicator described therein likewise allows for a comparably simple replacement of a clip magazine which can be detachably inserted through a lateral cutout in a tubular shaft of the clip applicator. Here, the clip magazine is designed as a disposable part, whereas a handgrip part and the tubular shaft which can be fastened thereto are configured as reusable parts. Further, this clip applicator offers the possibility to fasten different tubular shafts, which may differ from one another for instance in their shaft length, to a single handgrip part. Although this clip applicator allows for a relatively flexible handling, the application of different clip types still requires to change both the tubular shaft and the clip magazine. This is why it is still desirable to improve the handling of the clip applicator of the type described at the outset.

Further, the U.S. Pat. No. 6,599,298 B1 discloses a clip applicator comprising a handgrip part and a clip magazine which can be fastened thereto, both being designed as a disposable part. In this arrangement, the clip magazine is integrated in a shaft of the clip applicator and different shaft lengths allow to stock up or store a different number of clips and to apply them, if necessary. However, also this clip applicator does not offer the possibility to apply different clip types with the same clip applicator, so that the desire remains to improve the handling of the clip applicator of the kind described above.

SUMMARY

Starting from DE 20 2011 000 755 U1, the invention is based on the object to provide a surgical clip applicator which can be made available at comparably low costs and in which the handling is improved by use of constructional measures which are as simple as possible. Here, one aim is to improve the flexibility of the clip applicator in terms of the possible use of different clip types. A further/another aim is to be able to provide components of the clip applicator which are designed as disposable parts at the smallest possible costs.

This object is achieved by a universal handgrip, an individual clip magazine, as well as by a clip applicator including a universal handgrip and an individual clip magazine.

According to a first aspect of the present invention, a universal handgrip of a surgical clip applicator is suggested, to which an individual clip magazine, which comprises a crimping head and can be arbitrarily selected from a number of different clip magazines, can be mounted such that the universal handgrip and the individual clip magazine fastened thereto mechanically interact for crimping individual clips in the crimping head as well as for conveying individual clips from a clip receiving portion of the individual clip magazine via an individual feed path toward the crimping head. To this end, the universal handgrip comprises an integrated force transmission gearing or linkage comprising at least one manually graspable handle (handle lever, scissor handles) as an actuation-/input part and comprising a coupling means as an actuation-/delivery part to the individual clip magazine. According to the invention, an adaptation device is provided between the actuation-/input part and the actuation-/delivery part for compensating and accommodating clip-related differences between the individual feed path of the currently mounted individual clip magazine and the maximum actuating travel of the actuation-/input part on the universal handgrip.

This allows to equip the universal handgrip with a mechanical actuation system offering a certain maximum actuating travel/amount which is suitable for the application of those clips which are suitable for said maximum actuating travel/amount. If the situation arises that clips have to be applied which require a smaller actuating travel/amount, the adaptation device accomplishes a compensation or adaptation of the maximum actuating travel/amount with respect to the actuating travel/amount defined by the individual clip magazine. This allows to use the universal handgrip for different clips, too.

It is advantageous if the adaptation device comprises an overload protection means for interrupting the force transmission in the gearing preferably in the form of a sliding clutch or a releasing mechanism. In particular, the sliding clutch can be adjusted so as to have a slipping value which is above the force required for conveying individual clips from the clip receiving reservoir via the individual feed path toward the crimping head as well as below a predetermined actuating force overloading the force transmission gearing. In this way, there is no need to make any modifications on the force transmission gearing or the linkage (transmission ratio change etc.), so that the handling of the universal handgrip is simplified on the whole.

According to another aspect of the present invention, an individual clip magazine of a surgical clip applicator to be mounted to a universal handgrip of the clip applicator is suggested, comprising a crimping head, a clip receiving portion and a clip advancing means for conveying individual clips from the clip receiving portion via an individual feed path toward the crimping head depending on a manual operation of the universal handgrip. Here, provision is made that the individual clip magazine, which can be selected from a plurality of clip magazines for different clip types as needed, comprises an integrated coding mechanism which is formed depending on the clip type to be applied and with which at least the feed path adapted to the respective clip type is defined.

In other words, a coding mechanism is fixedly integrated in the different clip magazines, so that different clip magazines having different sizes/installation lengths and/or comprising different clip types can be used with one universal handgrip. In this context, the term "feed path" is to be understood as the route of transport for individual clips from a clip receiving portion/clip storage means of the clip magazine toward the crimping head.

Due to the fact that the coding mechanism for defining the feed path adapted to the respective clip type is integrated in the clip magazine, it is possible to (detachably) fasten a plurality of different clip magazines to a single (universal) handgrip, to replace them as needed and to apply the clips stored therein in each case. The clip magazines in a substantially shaft-like design may have different shaft lengths. Furthermore, different clip types may be stocked up in the different clip magazines, said clip types differing from one another for instance in terms of their shape and/or size and/or thickness. This means that a single (universal) handgrip can be combined with a plurality of different clip magazines (for instance two, three, four, five or more), to be able to apply different clip types while keeping the same handgrip.

Thus, the invention effectively improves the handling of the clip applicator and the spatial conditions in the surgery room, as one single handgrip allows, merely by an appropriate selection and a replacement of the clip magazine, to apply different clip types and to realize different shaft lengths of the clip applicator by merely replacing the clip magazine. Consequently, the invention also reduces the number of different clip applicators which have to be stored or made available in the surgery room. In this way, the invention contributes to the improvement of the clarity in the surgery room.

Further, the coding mechanism integrated in the respective clip magazine has the advantageous effect that there is a lower number of reusable handgrips which have to be sterilized after an operation.

It is preferred that the coding mechanism comprises a clip advancing means comprising at least one limiting stop which acts in the longitudinal direction of the clip advancing means and is intended for at least partially defining the feed path. In other words, the clip advancing means is a first essential part of the coding mechanism and ensures the feed path of the individual clips. By way of example, the clip advancing means may be designed as a clip advancing bar which is arranged or configured such that each manual operation of the handgrip by a user and the longitudinal movement caused thereby results in that always exactly one clip is received from the plurality of the clips stocked up in the clip magazine and is transported toward and into the application tool. In particular, the at least one limiting stop on the clip advancing means allows to limit a rearward and/or forward movement of the clip advancing means in the longitudinal direction of the shaft of the handgrip and hence to ensure the grasping of a single clip from the clip magazine and its transport toward the crimping head. In this case, the handgrip-side adaptation device comes into effect upon hitting the limiting stop. This means that an additional actuation of the handle lever is admitted in the case of a sliding clutch or a corresponding releasing mechanism, without said actuation being transferred to the individual clip magazine.

Another, possibly independent or additional aspect of the invention makes provision that the clip advancing means comprises two limiting stops which are spaced from each other in the longitudinal direction or the direction of movement of the clip advancing means, the positions and/or the distance of said limiting stops being adapted depending on the clip type to be applied such that a rearward and/or forward movement of the feed unit allows to take up exactly one clip from the clip magazine and to transport it exactly to the crimping head. The position of the limiting stops depends in particular on the size and/or thickness and/or shape of the clips to be applied, as well as possibly on the number of the clips to be stored in the clip magazine and/or the shaft length of the latter.

It has turned out to be advantageous if the at least one limiting stop is integrated in the clip advancing means as a cut and/or bent part in order to provide in this way a clip magazine which can be provided at comparably low costs. By way of example, the feed unit may be a sort of clip advancing bar which can be produced in low-cost manner from sheet metal or the like. The at least one limiting stop can then be stamped out on the sheet metal and bent up, if required. As an alternative to this, it is also conceivable to realize the clip advancing means as a plastic part comprising an integrated limiting stop.

A further, possibly independent or additional aspect of the invention makes provision that the coding mechanism of the clip magazine also comprises a crimping head (jaw part) which is adapted to the clip type to be applied. In other words, the crimping head adapted to the respective clip type by design may be an essential part of the coding mechanism of the clip magazine, in order to ensure the correct process of closing the clips during their application. This means that the coding mechanism, as an alternative or in addition to the limiting stop formed on the clip advancing means, may also comprise a crimping head matched with the clip type to be applied. This allows to reliably and safely apply and close different clip sizes, thicknesses or shapes and/or use shaft lengths without any adaptation of the (universal) handgrip part. In this case, the mechanical system provided within the magazine and intended for opening and closing the crimping head is correspondingly adapted as well, to be actuated via the handgrip. It is advantageous here if the mechanical actuation system associated to the crimping head and provided within the magazine requires a uniform actuating travel/amount for all different magazines, so that their actuation by the coupled universal handgrip does not require any adaptation device as is the case with the individual feeding means.

In a particularly advantageous embodiment of the invention, the crimping head comprises a guiding means which controls the closing and opening process and whose position and/or geometrical shape is adapted to the clip type to be applied and/or to the shaft length of the clip magazine. By way of example, the guiding means may be arranged on the crimping head or geometrically formed such that the closing movement of the crimping head with a comparably large clip differs from the closing movement of the crimping head with a comparably small clip. The mechanical actuation system associated to the crimping head and arranged on the magazine can then be standardized.

It has turned out to be advantageous if the crimping head of the clip magazine is adapted to come into contact with the at least one limiting stop of the clip advancing means in order to limit the rearward and/or forward movement of the clip advancing means. In other words, the crimping head of the clip magazine and the clip advancing means of the clip magazine can cooperate to the effect that always exactly one clip is taken from the clip magazine and transported toward the application tool.

According to a further, possibly independent or additional aspect of the invention, the handgrip comprises the above-mentioned overload protection means cooperating with the coding mechanism of the clip magazine, said overload protection means preventing the handgrip and/or of the clip magazine fastened thereto from being damaged due to excessively high actuation forces with a manual operation of the handgrip. This means that the flexible handling of the universally usable handgrip part is additionally improved by the measure that a (mechanical) overload protection means is fixedly integrated in the handgrip.

In a particularly cost-effective embodiment of the invention, the handgrip may be designed as a reusable part. This means that the handgrip which can be universally used with different clip magazines may be used repeatedly in several operations after sterilization.

For hygienic reasons, each of the plurality of clip magazines may be formed as a disposable part.

According to a further, possibly independent or additional aspect of the invention, the handgrip and/or the clip magazine may comprise a color-based and/or symbol-based coding which is adapted to the clip type to be applied and intended for visualizing the clip magazine which can be currently used with the universal handgrip. By way of example, a housing of the clip magazine may be colored with a color which is associated to a specific clip type. For the purpose of unambiguously associating the clip magazine to a handgrip which can be used with it, the handgrip may be provided with a correspondingly associable color coding means. This color coding means of the two combinable essential parts of the clip applicator allows an especially intuitive use of the clip applicator.

In summary, the invention makes provision that a surgical clip applicator consists of the handgrip and the clip magazine. The clip magazine is manufactured/provided as a component which is separate from the handgrip and can be detachably fastened/mounted to it as needed, with the handgrip and the clip magazine fastened thereto cooperating in order to form a tool for the application of individual clips and define a fixed feed path for the clip transport of individual clips from the clip storage means toward the crimping head of the magazine. According to the invention, the clip magazine which can be selected as needed from the plurality of different clip magazines for respectively different clip types comprises an integrated coding mechanism which is realized depending on the clip type to be applied, said coding mechanism defining at least the feed path adapted to an the respective clip type.

The handgrip may comprise an integrated shaft into which the clip magazine is inserted at least in part and where it may also be snapped in place, if need be. In each clip magazine from the plurality of clip magazines, a certain number of clips may be arranged or stocked up. The number of individual clips stored in the clip storage means may amount to approximately five to forty clips, preferably 20 to 30 clips. The individual clip magazines from the plurality of clip magazines differ from one another in that they can receive a different number of clips due to their size (installation length). Further distinguishing features of the individual clip magazines include the size/width, the design (U-shaped or V-shaped) and the caliper or thickness of the individual clips stored therein, which can be received in the respective clip magazine. By way of example, these different clips for distinction may be referred to as "small", "medium", "medium-large" or "large". The clip magazines from the plurality of clip magazines may also differ in terms of their shaft length to be achieved or in terms of the overall applicator length, which may amount to 240 mm, 290 mm or 340 mm, for example.

The universal handgrip may be configured, for instance, to be combined with a clip magazine which holds 20 clips in the size "small" and in the combined, i.e. assembled state results in an applicator length of 240 mm. The same handgrip may also configured to be combined with a clip magazine which holds 20 clips in the size "medium" and in the combined state results in an applicator length of 240 mm.

According to said combination scheme, at least and/or for instance the following tabularly illustrated combinations of universal handgrips with respective clip magazines for the assembly of a clip applicator are conceivable:

|  | Applicator length/Number of the clips | | |
| --- | --- | --- | --- |
| Clip size | Handgrip model 1 Handle 240 mm | Handgrip model 2 Handle 290 mm | Handgrip model 3 Handle 340 mm |
| Small | 240 mm/20 clips | | |
| Medium | 240 mm/20 clips | 290 mm/20 clips | |
|  |  | 290 mm/20 clips | |
| Medium-large |  | 290 mm/20 clips | |
| Large |  |  | 340 mm/20 clips |

BRIEF DESCRIPTION OF THE DRAWING FIGURES

Figure 2:
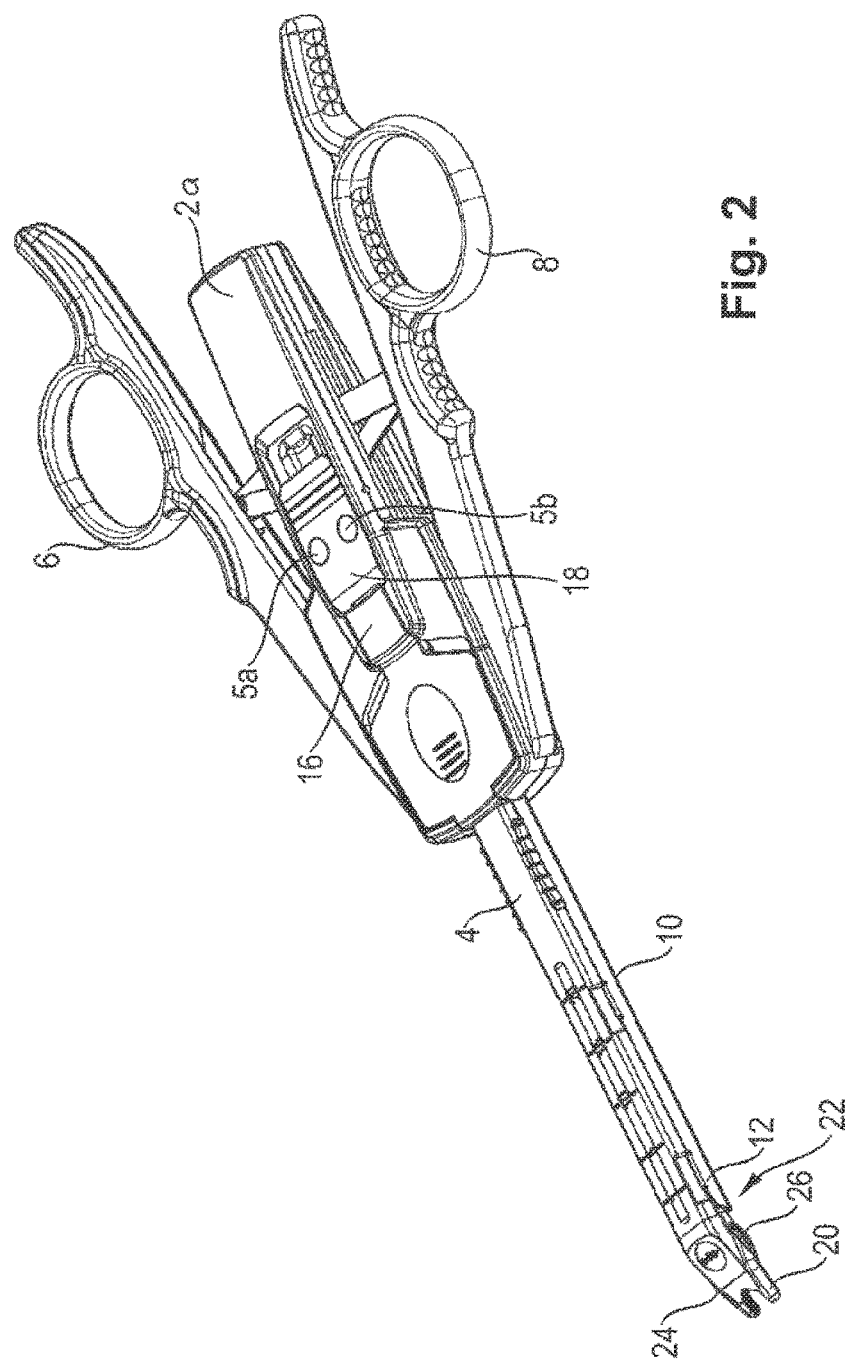
Figure 3:
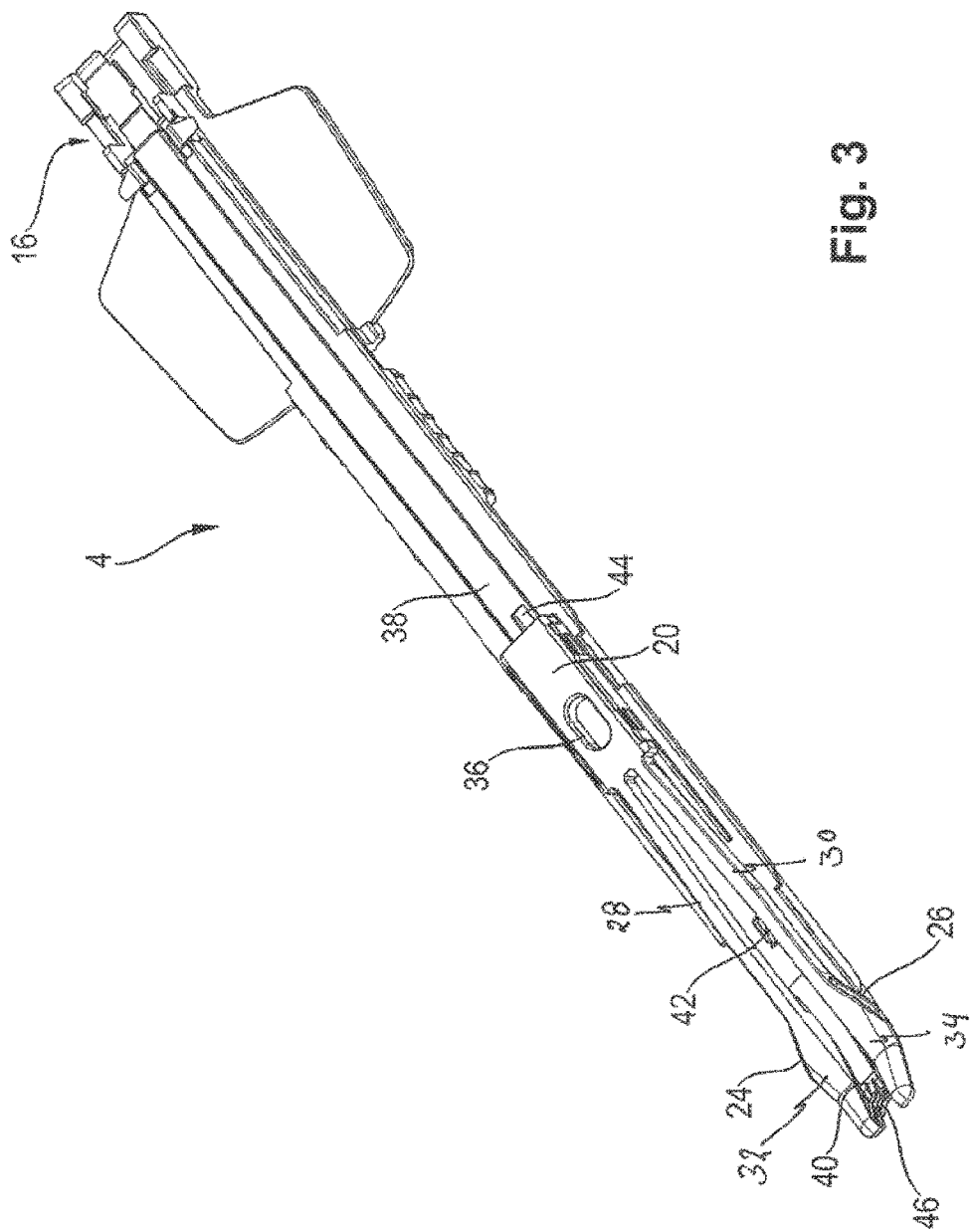
Figure 4:
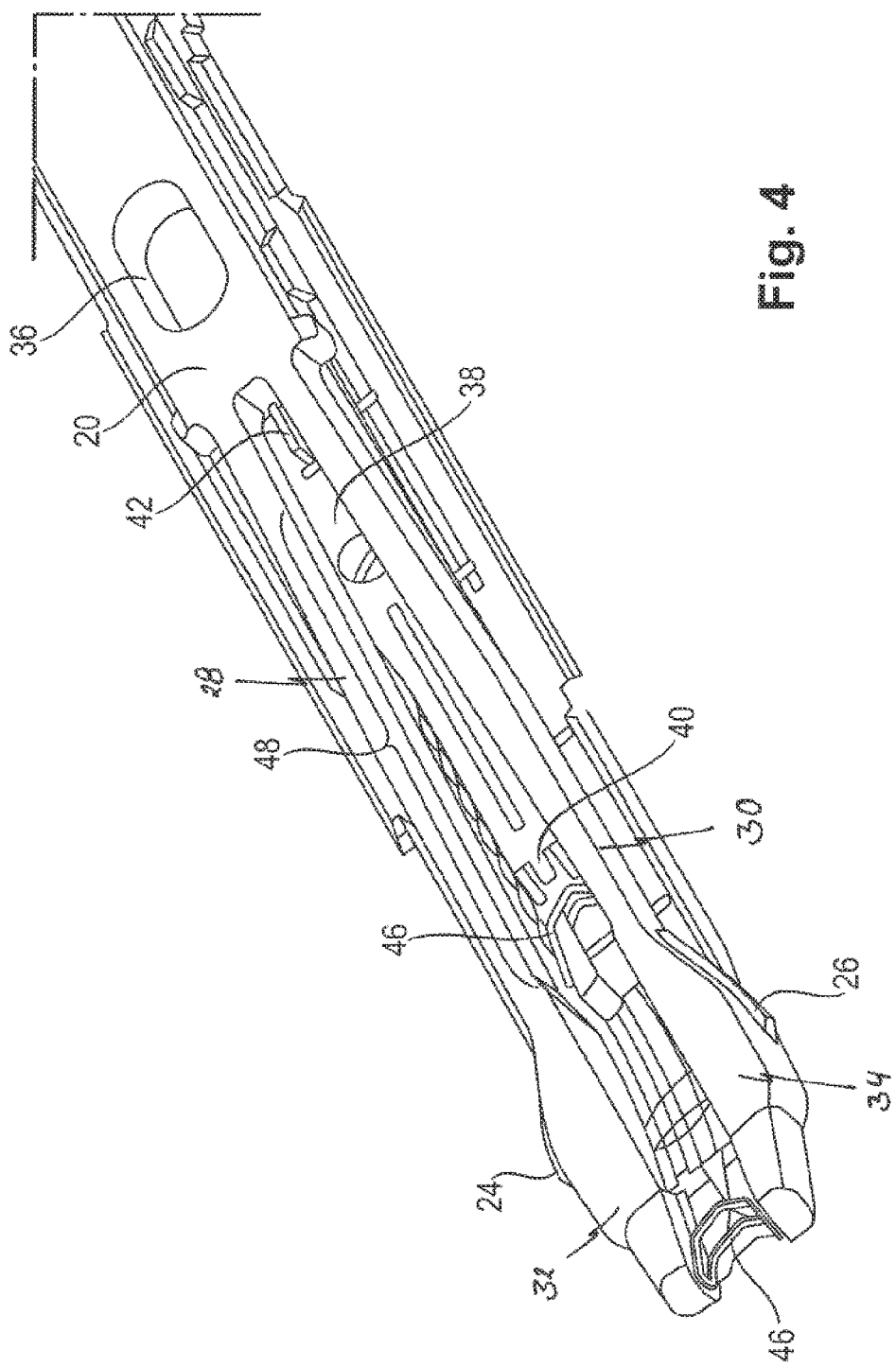
Figure 5:
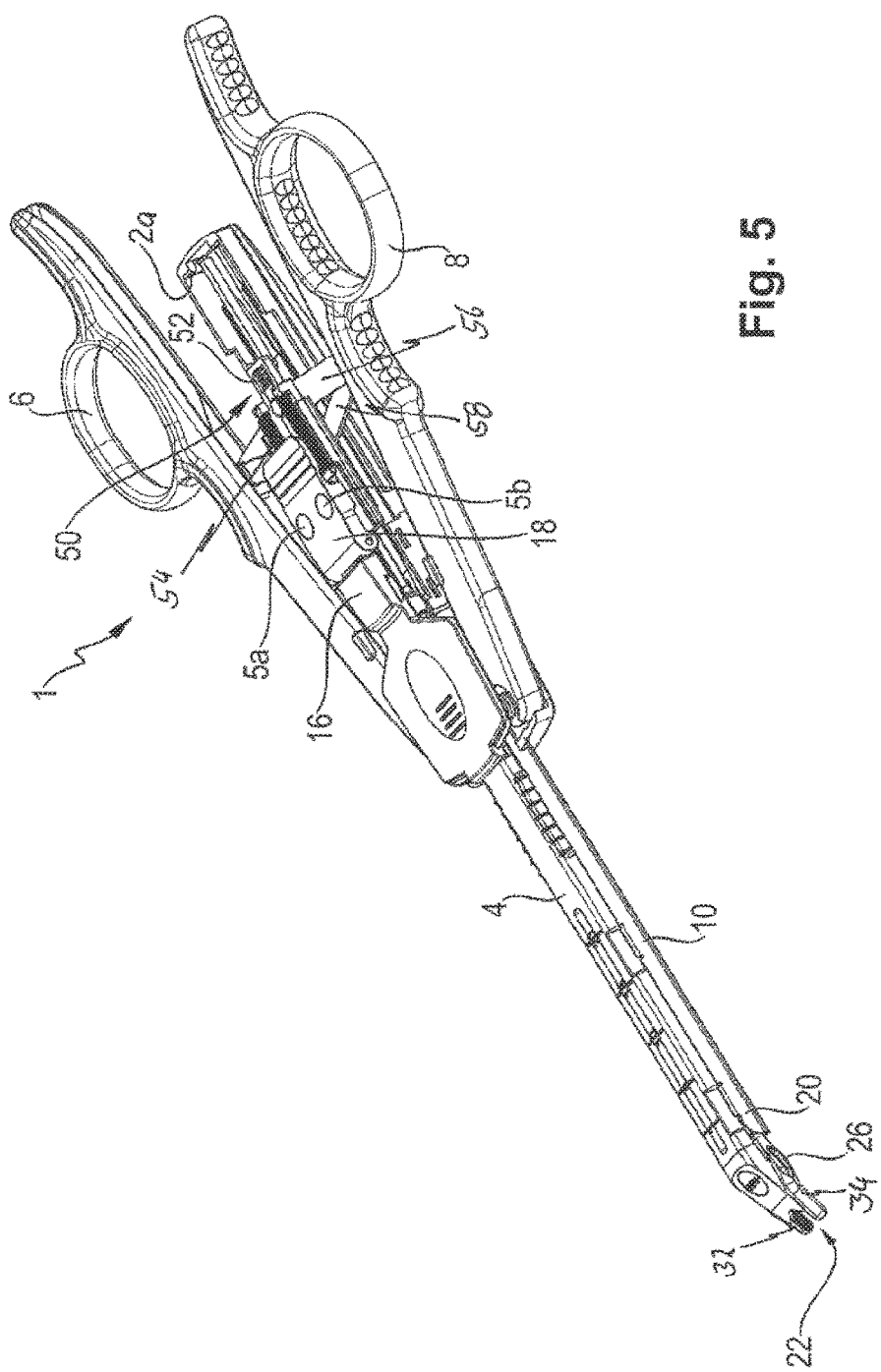

The invention will be explained in more detail below on the basis of a preferred exemplary embodiment with reference to the accompanying Figures in which:

FIG. 1 shows a perspective top view of a clip applicator according to the invention, consisting of a handgrip or handgrip part and a clip magazine which can be fastened thereto, FIG. 2 shows a perspective top view of the clip applicator according to the invention of FIG. 1 in an assembled state in which the clip magazine is detachably fastened to the handgrip part, FIG. 3 shows a perspective bottom view of a clip magazine according to the invention, being partly dismantled for illustration purposes, FIG. 4 shows a perspective bottom view of a segment of a clip magazine according to the invention, being partly dismantled for illustration purposes, and FIG. 5 shows a perspective side view of a clip applicator according to the invention, consisting of a handgrip part and a clip magazine fastened thereto and being partly dismantled for illustration purposes.

DETAILED DESCRIPTION

Identical or similar components are consistently provided with the same reference symbols.

FIG. 1 basically shows in a perspective top view a clip applicator (clip applicator set) 1 according to the invention, consisting of a universal (reusable) handgrip 2 and a number of separately selectable, individual clip magazines (for one-time use), from which an individual clip magazine 4 is exemplarily illustrated here. Such a clip applicator 1 may be used, for example, in open and/or endoscopic surgery in order to quickly and reliably connect tissue structures of a patient to each other or to pinch off blood vessels of a patient within short time and in a reliable manner.

The handgrip 2 according to the following detailed description and the essentially shaft-like clip magazine 4 according to the following detailed description are basically each arranged such that the clip magazine 4 selected from the plurality of clip magazines as needed can be detachably fastened to the handgrip 2, in order to jointly constitute the clip applicator 1 in this way. For illustration purposes, the handgrip 2 and the clip magazine 4 are shown here separate from each other.

Each clip magazine from the plurality of shaft-like clip magazines holds or stores a defined number of clips. A clip magazine usually contains approximately five to forty clips, preferably 20 to 30 clips. However, the individual clip magazines from the plurality of clip magazines differ from one another in that they can store different numbers of clips due to their size and overall length. Further distinguishing features of the individual clip magazines are also the size/width, the design (U-shaped or V-shaped) and the caliper or thickness of the individual clips which can be received in the respective clip magazine. The different clip magazines among the plurality of clip magazines may also differ in terms of their installation length, in particular in their shaft length.

The optional or need-based selection of a particular clip magazine 4 from the plurality of clip magazines for mounting to the handgrip 2 may be dictated, for example, by the structure of the tissue which has to be closed by staples or clips in the concrete case, or for instance also by the size of the blood vessels of the patient which have to be pinched off. In order to give the user an unequivocal indication which clip magazine 4 can/may be used for which handgrip 2, the handgrip 2 is provided with two marks 5a and 5b at least on the upper side facing the user, identifying the handgrip 2 as a handgrip piece which is arranged or configured for particular clip magazines 4. In this exemplary embodiment, the marks 5a, 5b are formed as circular, colored marks intuitively indicating the concrete embodiment of the handgrip part to the user/operator. In this exemplary embodiment, the universal handgrip 2 is an initially mentioned "handgrip model 1" for the clip sizes "small" and/or "medium" to be applied, being shown accordingly by the two colored marks 5a, 5b, for instance yellow for "small" and blue for "medium". Thus, a housing, preferably made of plastics, of the mating clip magazine 4 is colored or provided with color marks, in this exemplary embodiment in yellow color to identify the type of the clips which are stored or stocked up in the clip magazine 4 as "small".

Construction of the Handgrip

According to FIGS. 1 and 5, the handgrip 2 comprises a central housing 2a for receiving an actuation gearing 54 whose distal end portion is laterally provided with two articulated handle levers/scissors handles 6 and 8 as operating elements for manually operating the clip applicator 1 by an operator, for instance a surgeon, which are hinged such that the handle levers 6, 8 on both sides of the central housing 2a extend in proximal direction. The handle levers 6, 8 have proximal, free ends which each are constructionally adapted/approximated to the anatomy of a gripping hand of the operating doctor.

Furthermore, the handgrip 2 has its distal end portion (from the viewpoint of an operator) provided with a shaft 10 which has a U-shaped cross-section and is formed with the housing 2a in one piece or integrally connected thereto (material bond); integrated in the shaft is a crimping triggering device or closing device 12 in the form of a longitudinally movable, U-shaped slider and a retaining part 14 in the form of a bolt which is fixed (welded) to the shaft 10 and vertically protrudes from the base of the U-shaped handgrip shaft 10 in the lengthwise middle portion.

The exact way of functioning of the closing device 12 and of the retaining part 14 will be explained in detail below. In FIG. 1, however, it can be seen that the closing device 12 which is formed as a U-shaped slider has its lengthwise middle portion provided with a slot-like recess (cutout) 15 through which the bolt 14 protrudes, allowing a relative movement of the closing device (U-shaped slider) 12 with respect to the bolt 14 in the longitudinal direction of the handgrip shaft 10.

Moreover, the length and the width of the shaft 10 of the handgrip 2 are defined such that the substantially shaft-like clip magazine 4 can be at least partially inserted in the shaft 10 in such a manner that the handgrip 2 and the appropriately selected clip magazine 4 result in a total length of the clip applicator from 240 mm to 340 mm in the assembled state, in this exemplary embodiment a length of 240 mm.

According to FIGS. 1 and 5, a lock 18 which can be actuated from outside is supported on the housing 2a of the handgrip 2 so as to be movable in the longitudinal direction, the distal edge portion of said lock preferably forming a detent lug or ledge. Here, the lock 18 is preloaded in a distal direction by means of a spring into a locking position.

The two sides of the housing 2a facing the handle levers 6, 8 are provided with longitudinally extending slots where two conrods (tension/pressure rods) 56, 58 are inserted which connect the two handle levers 6, 8 to the actuation gearing 54 of the handgrip 2 and to the closing device 12. In the present case, the actuation gearing 54 consists of a preferably lock-shaped dog unit longitudinally displaceable relative to the closing device 12 and intended for a clip advancing means of an inserted clip magazine 4 described below.

Said dog unit preferably comprises an input element which is supported so as to be internally shiftable in the longitudinal direction; articulated to this input element is a conrod 56 each for coupling the two handle levers 6, 8 to the actuation gearing 54. Via an internal sliding clutch 52, the input element is in operative connection to an output element which is supported to be relatively shiftable in longitudinal direction and has its distal end provided with a latching/engaging portion for the clip advancing means of the currently inserted clip magazine 4. Here, the conrods 56 coupling the input element with the handle levers 6, 8 have an orientation in proximal direction starting from the handle levers 6, 8, in fact in such a manner that with a scissor-like compression of the two handle levers 6, 8, the input element and with this the output element (via the sliding clutch 52) is moved in proximal direction in the housing 2*a*.

In this process, it is to be noted that the entire dog unit according to the above-mentioned description is retained on the housing by means of a spring, so that it is elastically moved from the proximal position (pressed handle levers according to FIG. 2) toward the distal position (spread handle levers according to FIG. 1). Further, it is referred to the fact that the construction of the dog unit may also have a different design, as long as an actuating force applied to the handle levers 6, 8 via an adaptation device (overload protection means 50) corresponding to the exemplary input-output element sliding clutch unit is transferred to the latching/engaging portion so as to interrupt the flow of forces upon exceeding a predetermined actuating force and in this way make the handle levers 6, 8 move in inoperable manner (without any forces).

By means of a further conrod 58, both handle levers 6, 8 are coupled in each case to the closing device 12 in the form of the U-shaped slider supported in the handgrip shaft 10. These two additional conrods 58 have an opposite orientation with respect to the previously mentioned conrods 56, so that the U-shaped slider 12 is shifted in distal direction upon a scissor-like compression of the two handle levers 6, 8.

Construction of the Clip Magazine

Each of the clip magazines 4 according to FIGS. 1 and 4 has a shaft portion which can be inserted in the U-shaped shaft 10 of the handgrip 2 in respect of its dimensions and at the same time forms the clip receiving portion (clip storage means) of the magazine 4. For the purpose of detachably fastening/arresting it to the handgrip 2, the substantially shaft-like clip magazine 4 comprises a mounting device 16 which is provided on the proximal end of the shaft portion and cooperates with the lock (retaining device) 18 of the handgrip 2 in order to detachably lock/arrest the clip magazine 4 on the handgrip 2 which is (partially) inserted in the shaft 10 of the handgrip 2.

According to FIGS. 3 and 4, the distal end portion of the shaft portion of the clip magazine 4 is provided with a crimping tool 22 comprising a crimping head (jaw part) 20 which protrudes on the distal shaft end of the shaft 10 of the handgrip 2 from the latter when it is assembled with the handgrip 2. The crimping head 20 (in the following also referred to as a jaw part) is arranged to cooperate with the closing device 12 of the handgrip 2 formed as a U-shaped slider, in order to jointly form the crimping tool/crimping mechanism 22 of the clip applicator 1 on the distal end of the clip applicator 1.

For the cooperation with the closing device 12 formed as a U-shaped slider, the jaw part 20 (as seen in its longitudinal direction) has its left and right outer side provided with one (control) guiding means 24 and 26 each. The guiding means 24, 26 and the closing device 12 are each arranged to jointly define an opening and closing movement of the jaw part 20. Here, the position and the geometrical shape of the guiding means 24, 26 of the jaw part 20 can be or are individually defined for the different clip magazines from the plurality of clip magazines, in particular depending on the selected clip magazine and/or on the clip type to be applied, as a larger or smaller jaw opening is required on the crimping head 20 according to the clip magazine and/or clip type.

The opening and closing movement of the crimping heads/jaw part 20 is brought about if the closing device 12 formed as a U-shaped slider externally encloses the guiding means 24, 26 of the jaw part 20 at least partly during its longitudinal movement in the handgrip shaft 10, so that two inner surfaces (not shown in FIG. 2) of the U-shaped closing device 12 come into contact with the guiding means 24, 26 and hence also define or control the opening and closing movement of the jaw part 20. To this end, the jaw part 20 and the closing device 12 are each arranged or configured such that the closing device 12 formed as a U-shaped slider at least partially encloses the jaw part 20 which is fixed by means of the retaining part (bolt) 14 in the longitudinal direction of the shaft 10, if the two handle levers 6 and 8 are manually operated (compressed). This means that the closing device 12—upon operation of the handle levers 6, 8 by the previously indicated conrods 56, 58 of the handgrip 2—is moved or pushed lengthwise in distal direction of the clip applicator 1 so far forward in distal direction until the closing device 12 encompasses the guiding means 24, 26 of the jaw part 20 and thus forces the jaw part 20 to perform a closing movement. Due to this movement of the closing device 12, which is defined or controlled by the position and/or shape of the guiding means 24, 26, the jaw part 20 is closed and will be opened again after operation of the handle levers 6, 8 or by releasing them. The opening movement will be brought about by a (from distal view) rearward movement of the closing device 12 formed as a U-shaped slider.

FIG. 3 shows a perspective bottom view of the clip magazine 4, being partly dismantled for illustration purposes, or from which the individual components have been removed for the sake of a more demonstrative description.

It can be seen in FIG. 3 that the crimping tool 22 is substantially formed like a fork and comprises two branches 28 and 30 which are parallel to each other. At the free end of the crimping tool 22 pointing in the distal direction, said crimping tool comprises two integrally formed jaw part elements 32 and 34 where the above guiding means 24, 26 described above are arranged/formed and which constitute the jaw part (crimping head) 20. It can also be seen that the crimping tool 22 has its proximal end provided with a recess 36 as a fastening opening for the interlocking cooperation with the retaining part (bolt) 14 of the handgrip 2. In this exemplary embodiment, the recess 36 is implemented as an elongated hole which is engaged by the retaining part 14 of the handgrip 2 in the assembled state, in order to fix the crimping tool 22 (which is snapped in place in the shaft 10) in such a reliable manner on the shaft 10 that it can not move in the longitudinal direction of the clip magazine 4 and in the longitudinal direction of the shaft 10 of the handgrip part 2. In other words, the longitudinal position of the crimping tool 22 and hence of the jaw part 20 is defined by the cooperation of the recess 36 with the retaining part 14, so that it can neither move relative to the shaft 10 of the handgrip 2 nor to other components of the clip magazine 4.

The clip magazine 4 illustrated in FIG. 3 also comprises a clip advancing means 38 in the form of a clip advancing bar for receiving and supplying (i.e. transporting) separated clips. The clip advancing means 38 is arranged for a cooperation with the jaw part 20 and is shiftably supported relative to it in the longitudinal direction of the clip magazine 4 or in the longitudinal direction of the shaft 10 of the handgrip 2. This means that the feed unit 38 has the function to receive individual clips from the clip magazine 4 and to transport them onwards in the distal longitudinal direction of the shaft 10. To this end, the clip advancing means 38 has its distal end provided with a clip tongue 40 which is capable of receiving and supplying or transporting the individual clips.

For receiving the individual clips from the clip magazine 4, a rearward movement (from distal view) of the clip advancing means 38 is required, as the individual clips are positioned behind (from distal view) the jaw part elements 32, 34 for storing them. For this reason, the clip advancing means 38 has to perform a rearward movement so that it is positioned exactly behind (from distal view) the clip which is to be received next and fed or transported forward in the longitudinal direction of the shaft 10 toward the jaw part 20. On the other hand, for supplying or transporting the clips received by means of the clip advancing means 38 (from proximal view), a forward movement is required to move the received clip toward the jaw part 20, i.e. along the branches 28, 30 of the crimping tool 22 between the jaw part elements 32, 34 of it.

In order to limit these two longitudinal movements of the clip advancing means 38 in a simple manner, namely (from the proximal view) forward towards the jaw part 20 and (from the proximal view) rearward towards the clip receiving portion (clip storage means), the clip advancing means 38 comprises two limiting stops 42 and 44 which are spaced from each other in the longitudinal direction of it. The limiting stops 42, 44 are shaped and dimensioned such that they each can come into contact with the crimping tool 22 whose longitudinal position with respect to the clip advancing means 38 is defined by means of the retaining parts 14 engaging the recess 36. This means that the limiting stops 42, 44 hitting the crimping tool 22 depending on the situation limit the longitudinal movement of the clip advancing means 38 in both longitudinal directions.

In this exemplary embodiment, the limiting stops 42, 44 are implemented as a stamped/bent part in one piece with the clip advancing means 38. The distance in the longitudinal direction between the two limiting stops 42, 44 is sized or selected and defined such that the clip tongue 40—in the event of a (from the proximal view) rearward movement of the clip advancing means 38, i.e. in the course of a clip receiving movement of the clip feeding means 38—takes exactly one clip from the clip magazine 4, as will be explained in more detail below. FIG. 3 shows the clip advancing means 38 in a situation or position in which the proximal, i.e. the rearward limiting stop 44 as seen in the clip advancing means is in resting contact with the crimping tool 22. According to FIG. 3, the clip advancing means 38 is thus shown in a situation or position in which an individual clip 46 has been transported by means of the clip tongue 40 of the clip advancing means 38 toward the distal end of the jaw part 20, i.e. into the crimping tool 22 or is arranged therein.

It is obvious that the position of the clip advancing means 38 illustrated in FIG. 3 is (yet) not a position in which the jaws 32, 34 of the jaw part 20 for crimping the inserted clip are able to close. For closing the jaw part elements 32, 34, a rearward movement of the clip advancing means 38 is required beforehand, so that it does not stay fully between the jaw part elements 32, 34 in the illustrated position.

In FIG. 4, showing a perspective bottom view of a segment of the clip magazine 4 in a partially dismantled state, the clip advancing means 38 is illustrated in another situation/position in which it is able to receive an individual clip 46 from a clip storage portion 48 of the clip magazine 4 for supplying or forwarding it toward the jaw part 20 (crimping tool 22). It is to be seen that the clip storage portion 48 (from distal view) is arranged behind the jaw part elements 32, 34, so that an individual clip 46 (from distal view) has to be supplied or transported in forward direction to convey it between the jaw part elements 32, 34.

Further, it can be seen in FIG. 4 that the clip advancing means 38 in the illustrated clip receiving position rests on the crimping tool 22 with the distal limiting stop 42, i.e. the forward one in the clip advancing means, whereby the clip receiving movement is limited in this direction of movement. The positioning of the limiting stop 42 which is dimensioned and correspondingly defined depending on the clip magazine 4 ensures that always only one single clip 46 is taken from the clip storage means 48 of the clip magazine 4 and, in a subsequent clip feeding movement in the clip advancing direction is transported toward the distal end of the crimping tool 22, i.e. between the jaw part elements 32, 34 and into in the jaw part 20.

In FIG. 5, which shows a perspective side view of the clip applicator 1 in a partially dismantled state, one can see that the handgrip 2 of the clip applicator 1 comprises the integrated overload protection means 50 including the sliding clutch 52. The overload protection means 50 (including the sliding clutch 52) prevents the mechanical parts of the handgrip 2 and/or the mechanical parts or housing parts of the clip magazine 4, or also the limiting stop 42 itself or the jaw part 20, from being damaged by excessively high actuation forces of the operator if the forward limiting stops 42 hit the crimping tool 22. As the distances between the limiting stops 42, 44 of the clip magazine 4 for the different clip magazines from the plurality of clip magazines are positioned or defined to be different, the overload protection means 50 may additionally ensure that a universal handgrip 2 can cooperate with several magazines from the plurality of clip magazines without damaging the mechanical parts or the components of the respective handgrip 2 and/or of the respective clip magazine 4 due to excessively high manual actuation forces.

The operation and the practical use of the clip applicator 1 may proceed as described in the following.

FIG. 2 shows in a perspective side view the clip applicator 1 in the assembled, i.e. in the operative state in which the clip magazine 4 is fastened by the cooperation of the mounting device 16 and the retaining device 18.

Having assembled the clip applicator 1 by mounting the clip magazine 4 (which has been selected as needed) to the universal handgrip 2, the clip applicator 1 is in an operative state. This means that in this state the clip magazine 4 is inserted in the handgrip shaft 10 and arrested by means of the lock 18.

A manual operation of the two handle levers 6 and 8 of the handgrip 2 activates the actuation gearing 54 of the handgrip 2 in such a manner that the closing device 12 realized as a U-shaped slider is longitudinally displaced in the distal direction. Due to this longitudinal displacement of the closing device 12, the latter is pushed over the guiding means 24, 26 of the jaw part 20, whereby its jaw part elements 32, 34 are pressed toward each other (i.e. in inward direction) and thus the crimping tool 22 is closed.

On the other hand, the actuation gearing 54 of the handgrip 2 is simultaneously also actuated in such a manner that the clip advancing means 38 is shifted in a longitudinal movement (in proximal direction) opposite to that of the closing device 12 until the forward limiting stop 42 hits the fixed crimping tool 22 and the sliding clutch 52 of the overload protection means 50 is triggered, as the case may be. The actuation gearing 54 of the handgrip 2 retains the clip advancing means 38 in this position until the jaw part elements 32, 34 will again be spaced from each other by pushing back the closing device 12 and hence the crimping tool 22 is opened again. With this, a clearance is created between the jaw part elements 32, 34 again, the clip advancing means 38 being (automatically) released by means of the actuation gearing 54 and the next clip being able to be transported by a spring bias-supported forward movement of the clip tongue 40 between the jaw part elements 32, 34.

In summary, a surgical clip applicator is disclosed which comprises a universal handgrip and an individual clip magazine having an integrated crimping head, which individual clip magazine can be detachably fastened to the universal handgrip. The universal handgrip and the individual clip magazine fastened thereto interact in order to form a feed path for the clip transport of individual clips from a clip receiving portion of the clip magazine toward the crimping head, which feed path is defined or individually available for actuation. According to the invention, the individual clip magazine can be selected from a plurality of clip magazines for different clip types as needed, wherein the clip magazine an integrated coding mechanism designed depending on the clip type to be applied, which coding mechanism defines at least the feed path adapted to the respective clip type in interaction with the universal handgrip.

The invention claimed is:

1. A surgical clip applicator comprising:
   an individual clip magazine being formed as a separate unit; and
   a universal handgrip to which the individual clip magazine being arbitrarily selected from a number of different types of clip magazines, can be detachably mounted or fastened,
   wherein the individual clip magazine comprises:
   a crimping head or crimping tool at a distal end portion;
   a clip receiving portion provided proximal to the crimping head or crimping tool;
   a clip advancing device for conveying individual clips from the clip receiving portion via an individual feed path toward the crimping head or crimping tool;
   a magazine-integrated coding comprising two limiting stops defining the individual feed path thereby limiting the clip advancing device in its conveying movement, which limiting stops are formed and positioned depending on the clip type to be applied; and
   a proximal end portion on the individual clip magazine, the proximal end portion on the individual clip magazine being adapted to detachably lock or arrest the individual clip magazine in the universal hand grip, and
   wherein the universal handgrip comprises:
   an integrated force transmission gearing comprising:
   at least one manually graspable handle as an actuation-/input part; and
   a coupling element as an actuation-/delivery part to the individual clip magazine, for which the coupling element is adapted to become interconnected with the clip advancing device when the individual clip magazine is mounted and locked/arrested in the universal handgrip by said proximal end portion on the individual clip magazine; and
   an overload protection clutch in form of a sliding clutch for interrupting the force transmission in the gearing between the at least one manually graspable handle and the coupling element when the clip advancing device is limited in its conveying movement by one of said two limiting stops.

2. The surgical clip applicator according to claim 1, wherein the overload protection clutch of the universal handgrip is designed for the purpose that the feed path adapted to the respective clip type is defined by a coding which is integrated in the currently mounted individual clip magazine and formed depending on the clip type to be applied.

3. The surgical clip applicator according to claim 1, wherein the sliding clutch of the universal handgrip is adjusted so as to have a slipping value which is above the force required for conveying individual clips from the clip receiving reservoir via the individual feed path toward the crimping head or crimping tool as well as below a predetermined actuating force overloading the force transmission gearing.

4. The surgical clip applicator according to claim 1, wherein the sliding clutch of the universal handgrip is configured to interrupt transmission force between the at least one handle and the coupling element in response to compression force applied to the at least one handle.

5. The surgical clip applicator according to claim 1, wherein the two limiting stops comprises at least one limiting stop which acts in the longitudinal direction of the clip advancing device and is intended for at least partially defining the feed path.

6. The surgical clip applicator according to claim 1, wherein the two limiting stops which are spaced from each other in the longitudinal direction or the direction of movement of the clip advancing device, the positions of said limiting stops being adapted depending on the clip type to be applied such that a rearward and/or forward movement of the feed unit allows to transport exactly one clip from the clip magazine toward the crimping head or crimping tool.

7. The surgical clip applicator according to claim 1, wherein the clip advancing device of the individual clip magazine is a rod which is supported to be movable in the longitudinal direction and is realized in the form of a plate, with the at least one limiting stop being integrated in the rod as a cut and/or bent part.

8. The surgical clip applicator according to claim 1, wherein the crimping head or crimping tool is adapted to come into contact with at least one of the two limiting stops of the clip advancing device in order to limit a rearward and/or forward movement of the clip advancing device.

9. The surgical clip applicator according to claim 1, wherein the universal handgrip is designed as a reusable part.

10. The surgical clip applicator according to claim 1, wherein the individual clip magazine is designed as a disposable part.

11. The surgical clip applicator according to claim 1, wherein the universal handgrip and the individual clip magazine comprise a color-based and/or symbol-based coding which is adapted to the clip type to be applied and intended for visualizing the individual clip magazine currently used with the universal handgrip.

* * * * *